US007773074B2

(12) United States Patent
Arenson et al.

(10) Patent No.: US 7,773,074 B2
(45) Date of Patent: Aug. 10, 2010

(54) MEDICAL DIAGNOSTIC IMAGING THREE DIMENSIONAL NAVIGATION DEVICE AND METHODS

(75) Inventors: James W. Arenson, Woodside, CA (US); John I. Jackson, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1152 days.

(21) Appl. No.: 11/170,323

(22) Filed: Jun. 28, 2005

(65) Prior Publication Data

US 2007/0016025 A1 Jan. 18, 2007

(51) Int. Cl.
*G06F 3/041* (2006.01)
(52) U.S. Cl. ........................................ 345/173; 600/443
(58) Field of Classification Search ................ 600/443; 345/156–184
See application file for complete search history.

(56) References Cited

U.S. PATENT DOCUMENTS

| 5,454,371 | A | * | 10/1995 | Fenster et al. ................ 600/443 |
| 5,841,440 | A | | 11/1998 | Guha |
| 5,923,318 | A | * | 7/1999 | Zhai et al. .................... 345/157 |
| 6,009,210 | A | | 12/1999 | Kang |
| 6,014,142 | A | | 1/2000 | LaHood |
| 6,181,343 | B1 | | 1/2001 | Lyons |
| 6,271,842 | B1 | | 8/2001 | Bardon et al. |
| 6,314,312 | B1 | * | 11/2001 | Wessels et al. ............... 600/427 |
| 6,317,621 | B1 | | 11/2001 | Graumann et al. |
| 6,346,938 | B1 | | 2/2002 | Chan et al. |
| 6,424,410 | B1 | | 7/2002 | Pelosi |
| 6,484,049 | B1 | | 11/2002 | Seeley et al. |
| 6,490,475 | B1 | | 12/2002 | Seeley et al. |
| 6,734,884 | B1 | | 5/2004 | Berry et al. |
| 6,738,044 | B2 | * | 5/2004 | Holzrichter et al. .......... 345/158 |
| 6,757,068 | B2 | | 6/2004 | Foxlin |
| 2002/0113775 | A1 | * | 8/2002 | Spencer ....................... 345/164 |
| 2003/0179177 | A1 | * | 9/2003 | Wang .......................... 345/156 |
| 2003/0206152 | A1 | * | 11/2003 | Shih et al. .................... 345/163 |
| 2004/0171922 | A1 | | 9/2004 | Rouet et al. |
| 2004/0239622 | A1 | | 12/2004 | Proctor et al. |

FOREIGN PATENT DOCUMENTS

GB       2414309 A   * 11/2005

OTHER PUBLICATIONS

"The Cubic Mouse: A New Device For Three-Dimensional Input," by Bernd Frohlic and John Plate; ACM Press, New York, New York; Conference on Human Factors in Computing Systems Proceedings of the SIGCHI Conference on Human Factors in Computing Systems; The Hague, The Netherlands, pp. 526-531; 2000.
"The Cubic Mouse: A New Device For Three-Dimensional Input," by Bernd Frohlic and John Plate; ACM Press, New York, New York; Conference on Human Factors in Computing Systems Proceedings of the SIGCHI Conference on Human Factors in Computing Systems; The Hague, The Netherlands, pp. 526-531; 2000. (Full text).

* cited by examiner

*Primary Examiner*—Long V Le
*Assistant Examiner*—Saurel J Selkin

(57) ABSTRACT

A physical 3D volume object is manipulated to navigate through a volume image. The orientation of the volume object, such as a cube or other shaped device, is sensed. As the volume object is rotated, the viewing direction associated with three dimensional rendering rotates. The volume object may represent a viewer's eye or the object for determining the viewing direction from the volume object orientation. The volume object may be untethered and/or generally flat, allowing ease of use. The volume object may be associated with a shape of an organ or tissue to provide further frame of reference.

19 Claims, 1 Drawing Sheet

MEDICAL DIAGNOSTIC IMAGING THREE DIMENSIONAL NAVIGATION DEVICE AND METHODS

BACKGROUND

This present invention relates to three dimensional (3D) navigation for imaging. For example, navigation devices and methods are provided for controlling the viewing perspective in 3D rendering of medical images.

One challenge of rendering 3D images on two dimensional display monitors is providing the viewer convenient access to all of the three dimensional (volume) data. Navigation is provided though control knobs, a mouse, a joystick, and/or software (graphic) navigation devices. In one approach, a 2D graphical model or icon on the display is manipulated via the mouse. For example, a 2D model or "virtual mouse pad" representing the surface of an organ (e.g. heart ventricle) is displayed. A mouse moves a pointer along this virtual surface to navigate through the 3D volume image. In other approaches, the user's body or major parts of the body are tracked for navigation. For example, head motions, whole body gestures or the movement of principle body parts are detected from video images. As another example, a 3D touch pad (i.e. a touch pad that has shapes or curves along which a user can slide his finger) is used to navigate. In yet other approaches, a surgical instrument or tool is used to manipulate or align the 3D image.

These approaches may not offer a natural or intuitive control of the volume visualization, making it difficult to quickly and precisely view a rendered volume image. These approaches may require a long learning curve to get accustomed to the controls, and even then, often provide imprecise and awkward navigation.

BRIEF SUMMARY

By way of introduction, the preferred embodiments described below include methods, devices and systems for three dimensional navigation, such as navigation for medical diagnostic ultrasound imaging. The orientation of a volume object, such as a cube or organ shaped object, is sensed. As the device is rotated, the viewing direction associated with three dimensional rendering rotates. The device represents the object for determining the viewing direction from the device orientation, more likely providing a natural or intuitive user interface for navigation. Alternatively, the device may represent a viewer's eye for navigation. The device may be untethered and/or have generally flat surfaces, allowing ease of use. The device may be associated with a shape of an organ or tissue to provide further frame of reference.

In a first aspect, a system is provided for three dimensional navigation with medical diagnostic ultrasound imaging. A medical diagnostic ultrasound system is operable to generate a three dimensional representation of an ultrasonically scanned region. A sensor (e.g., a transponder) is provided on a volume object, the medical diagnostic ultrasound system or both the volume object and the medical diagnostic ultrasound system. The sensor (e.g., a transponder) is operable to determine an orientation in three-dimensions of the volume object. The medical diagnostic ultrasound system generates the three dimensional representation as a function of a viewing angle responsive to the orientation or position.

In a second aspect, a device is provided for three dimensional navigation with medical imaging. A volume object has an organ or body part shape. A sensor device, such as a transponder, for determining an orientation and/or position in three-dimensions of the volume object is on or in the volume object.

In a third aspect, a system is provided for three dimensional navigation with volume imaging. A volume object has a generally flat outer surface. A sensor is operable to determine an orientation in three-dimensions of the volume object. An imaging system is operable to generate a three dimensional representation. The three dimensional representation is displayed as a function of a viewing angle responsive to the orientation and/or position.

In a fourth aspect, a system is provided for three dimensional navigation with volume imaging. A volume object is without a tether. A sensor, such as a transponder, is operable to determine an orientation in three-dimensions of the volume object. An imaging system is operable to generate a three dimensional representation. The three dimensional representation is displayed as a function of a viewing angle responsive to the orientation and/or position.

In a fifth aspect, a method is provided for three dimensional navigation with volume imaging. An orientation of a volume object is sensed. A three dimensional representation is rendered as a function of the orientation. The orientation represents an eye orientation of a viewer.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A physical 3D volume object is manipulated to navigate through a volume image, modeling the natural way people interact with or examine physical objects. Using an untethered volume object with a size and shape that allows precise and natural control involves the same human motor control that would be involved if the user were looking at a real object in space. This physical volume object is a direct analog of either a graphic cube rendered along with the rendered volume on the display or a representation of the 3D structure that is being rendered. The volume object encapsulates transponders or other sensor devices, such as reflectors. The volume object is manipulated by hand near the 3D image display. The orientation and/or position of the cube is detected and used by the image rendering system to display the 3D image corresponding to the position and orientation of the volume object.

Figure 1:
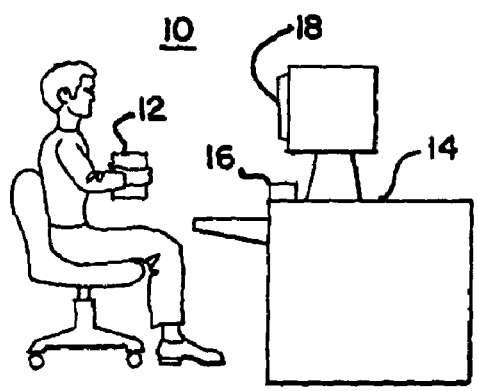
FIG. 1 is a side view representation of one embodiment of a volume object in use with an imaging system.

FIG. 1 shows a system 10 for three dimensional navigation with volume imaging. For example, the system 10 is for three dimensional navigation with medical imaging, such as medical diagnostic ultrasound imaging. The system 10 may be used for other imaging applications, such as for Magnetic Resonance Imaging (MRI), computed tomography (CT), positron emission tomography (PET) or other medical 3D imaging modalities. CAD workstations, video games or virtual reality applications, such as medical or non-medical imaging, may use the system 10. Data mining where multi-dimension data sets are converted into homomorphic terrains or other volume metaphors may use the system 10.

The system 10 includes a volume object 12, an imaging system 14 with a display 18, and a sensor 16. Additional, different or fewer components may be provided. For example, additional sensors 16 are provided. As another example, other user inputs devices, such as a keyboard or mouse, are provided in addition to the volume object 12 and the sensor 16.

Figure 2:
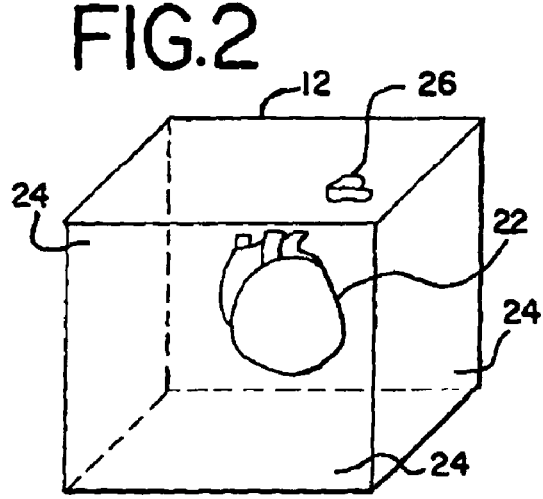
FIG. 2 is a graphical representation of one embodiment of a volume object.

The volume object 12 is metal, wood, plastic, rubber, foam, acrylic, fiberglass, glass, combinations thereof or other now known or later developed material. The volume object 12 is shaped or sized for handheld use. For example, a greatest dimension is less than six inches. The volume object 12 is sized small enough to fit comfortably in a user's hand, and large enough to allow operation of the sensor 16 (i.e., allow adequate position or orientation resolution). For example, the volume object 12 is an approximately 40 mm×40 mm×40 mm cube as shown in FIG. 2. Alternatively, other sizes are provided.

The volume object 12 has a generally flat outer surface. As a cube or spheroid without protrusions, the volume object 12 has a flat outer surface. Flat is used herein as without protrusion rather than planar. Corners and edges may be rounded for comfort. In another embodiment, the volume object 12 is shaped as an organ (e.g., a heart) or other body part. As shown in FIG. 2, buttons 26 or other substantially flush user inputs are provided while maintaining generally flat surfaces. Alternatively, the buttons 26 or controls can be separate from the volume object 12, such as being located on the system, on a keyboard or on a joystick. The object shape 12 is without adjustable parts in another embodiment, such as being without rods that extend into, out of or flip up from generally flat surfaces. Non-flat or surfaces with protrusions may be used.

The volume object 12 is clear (e.g., transparent), opaque or both. For example, the volume object 12 has a transparent outer surface, such as a clear cube, with an organ icon 22, direction icon or both organ and direction icons within the volume object 12. Using clear acrylic or other material, the contents of the volume cube 12 may be seen. The organ icon 22 is a volume image, wire frame, etching, projection or other image representing a volume or organ to be scanned. The organ icon 22 within the volume object 12 provides a frame of reference for a user orienting the volume object 12 as an input to orient 3D rendering. In the case of echocardiography, a small heart shape is encapsulated to provide the up/down and front/back visual cues. Similarly, if the primary targeted application involves some other organ, then a small model of that organ is encapsulated. Instead of specific organs, a small human model shape offers a generic model, used to orient up/down and left/right. Alternatively or additionally, a direction icon, such as a plastic arrow or other pointer cast into the volume object 12 indicates an "up" or other direction. Additional direction icons may be incorporated to indicate front/back or left/right.

Alternatively or additionally, the volume object 12 is shaped, painted or shaped and painted similar to an organ to be represented by the three dimensional representation. Organ shaped models, a generic shape with icons painted on the surface, a generic shape with the surface painted to represent an organ or combinations thereof may be used. Painting includes screen printing or other processes for coloring a surface. Direction icons are additionally or alternatively provided on the outside surface of the volume object 12.

The volume object 12 is free of physical connection, such as being without a tether or cord. Any power is provided by one or more batteries in the volume object 12, and any communications are provided wirelessly. The volume object 12 may be free of electronics, such that power and a tether are not provided. Alternatively, the volume object 12 connects with a cord to the sensor 16 and/or the imaging system 14 for power and/or communications.

A user input is optionally provided on the volume object 12. For example, the button 26 is on a surface of the volume object 12. Capacitive sensors, membranes, touch pads, sliders, knobs, pressure sensors, motion activated switch, combinations thereof or other now known or later developed user inputs may be used. For example, tapping the volume object 12 activates or deactivates functions using a motion activated or pressure switch within the volume object 12. The user input is operable to activate orientation sensing, cut-plane sensing, position sensing or combinations thereof. The user input device allows the user to signal the system 10 when navigation is active or inactive. When deactivated, a user can move the volume object 12 without the system 10 responding. This navigation on/off control is used when the volume object 12 is retrieved or returned to a resting location, or simply when the volume object 12 is held by the user but not needed for navigation. A timer may avoid early activation, such as when a user grabs the volume object 12 but does not want the position changes to provide navigation inputs immediately. Alternatively, the user input may, in part or whole, be positioned on or near the imaging system 14, the sensor 16 or other control mechanism.

The imaging system 14 is a medical diagnostic ultrasound, MRI, CT, PET or other imaging system. For example, the imaging system 14 connects or includes one or more scanning devices for acquiring data representing a volume within a patient, such as representing the heart of the patient. Ultrasound may be used to generate a sequence of real-time 3D representations (i.e., four dimensional imaging). Alternatively, the imaging system 14 is a workstation, computer or other device for generating 3D representations from data acquired with other systems. In yet another alternative embodiment, the imaging system 14 generates the 3D representation from a local or remote memory of data.

The imaging system 14 generates a three dimensional representation. For example, the imaging system 14 is a medical diagnostic ultrasound imaging system operable to generate a 3D representation of an ultrasonically scanned region. The 3D representation is rendered as a function of a viewing angle. Maximum, minimum, alpha blending or other ray line based rendering is performed. Surface or texture rendering from a viewing angle is alternatively performed. Cut plane or multiple plane rendering may be used. The resulting 3D or 2D representation is displayed as a function of a viewing angle. The viewing angle is input by the user, such as by orienting the volume object 12. For example, the medical diagnostic ultrasound imaging system 14 generates the 3D representation by rendering along ray lines at a viewing angle of the volume object 12 to the user or the imaging system 14.

In one embodiment, a representation or graphic 32 (see FIGS. 3 and 4) of the volume object 12 is also rendered. The position and/or orientation information passed to the 3D rendering software is interpreted and used to locate and display a graphical cube, other wire frame or shaded surfaces on the display 18 representing the volume object 12 and current orientation of the volume object 12. The 3D image 34 is presented inside or associated with this graphic 32. As the user moves the volume object 12 in their hand, the new position and/or orientation is detected. The graphic 32 and the displayed 3D image 34 move to the new position and/or orientation. Alternatively, the 3D image 34 is displayed without the graphic 32. For versatility, the system SW may be configured such that the user can disable or enable the graphic 32.

The sensor 16 is an optical sensor, an acoustic sensor, an accelerometer, a magnetic sensor, a radio frequency sensor or combinations thereof. The sensor 16 may be responsive to one or more sensed devices 24, such as reflectors, transponders or antenna. Alternatively, the sensor 16 senses the outer surface of the volume object 12 or an icon 22 within the volume object, such as with a video sensor or camera. The sensor 16 senses a property, such as time of a reflected wave or a signal from a transponder. The sensor 16 may be a transponder, such as sensing a wave and sending a transmission in response to the wave.

The sensor 16 is on or adjacent to the imaging system 14, but is alternatively or additionally on the volume object 12. For example, the sensor 16 is a video camera and software for identifying an orientation and/or position of the volume object 12. As another example, three or more transponders 24 are positioned on the volume object 12. Optical, acoustic, or radio frequency (RF) position sensing sense the relative positions of the transponders 24. One implementation uses three miniature microphones as position transponders 24 mounted in the volume object 12. These microphones detect very high frequency acoustic "pings" generated from either a single or several acoustic speakers located on and controlled by the imaging system 14. These detected pings are transmitted back to the system using a Bluetooth, radio frequency, acoustic or other channel. The relative arrival times of the pings at the transponders 24 on the volume object 12 and/or at the imaging system 14 are used to calculate (triangulate) the position of the three transponders, providing the position and/or orientation of the volume object 12. As another example, the sensor 16 is on volume object 12 and wirelessly communicates the position or orientation information to the imaging system 14.

Figure 3:
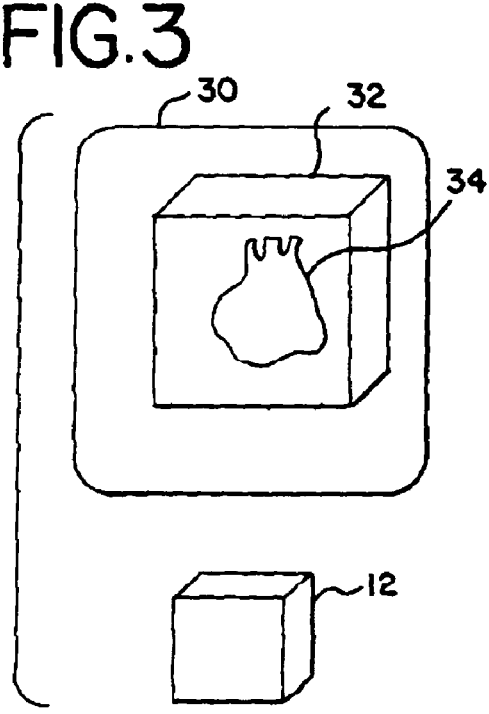
FIGS. 3 and 4 are example graphical representations showing a relationship between a volume object orientation and a three dimensional image representation.
Figure 4:
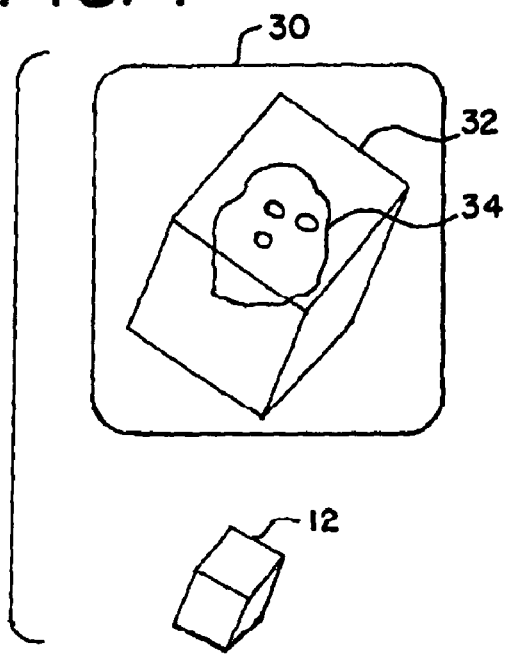

The sensor 16 determines an orientation and/or position in three-dimensions of the volume object 12. FIG. 3 shows the volume object 12 in a first position, and FIG. 4 shows the volume object 12 in a different position. The 3D representations 34 and corresponding graphics 32 are rendered on the display 30 as a function of the orientation of the volume object 12.

The sensor 16 senses only orientation, only position, or both orientation and position. The orientation and/or position are around or along one, two or three axes or dimensions. For example, orientation is used to determine viewing direction for rendering. The orientation of the volume object 12 is directly mapped to the orientation of the displayed 3D image 34 and any graphic 32. The distance towards or away from a portion of the medical diagnostic ultrasound system 14 or from the sensor 16 is used as input of an amount of zoom of the 3D image 34. The detected distance controls magnification. Moving the volume object 12 away from the user (i.e. closer to the display screen) is interpreted to reduce the size of the displayed volume, or "zoom out." Moving the volume object 12 closer to the user is interpreted to increase the size of the displayed volume or to "zoom in." Up/down and left/right movements of the volume object 12 are ignored such that the rendered 3D image 34 remains centered in the display 30.

In another embodiment, the position along the three dimensions is sensed. Cut-planes of the scanned region are rendered, selected and/or displayed as a function of the position. The user presses a control button to signal the system 14 that cut planes are being adjusted. While the button is pressed or after pressing the button, subsequent movements of the volume object 12 in x, y and z are interpreted to move the imaged volume in the corresponding direction while maintaining the graphic 32 or volume in a fixed position relative to the display 30. As the imaged volume moves outside the graphic 32 or displayed volume, a planar surface or cut plane at the edge of the graphic 32 is rendered. While in this "cut plane" navigation mode, the system responds only to displacements in x, y and z, but may also respond to rotation or changes in orientation. After releasing or again activating the control button, the imaging system 14 returns to the original navigation mode and once again responds to motions by changing the orientation and/or zoom.

In a similar way to managing cut planes, the volume object 12 is alternatively or additionally used to control multi-planar reconstruction images, such as multiple cut planes (e.g., cut planes along defined axes) and/or a cut plane arbitrarily oriented in space. Another button is pressed to signal that motions or change of position of the volume object 12 are now mapped to the multi-planar reconstruction axes. Changes in orientation rotate the axes in the corresponding way. Changes in distance of the cube from the face of the display 30 map to magnification or zoom. Alternatively, changes in x, y and/or z coordinates define intersections for the cut planes. A "center" or "reset" control button or function may be used when cut planes are no longer needed or to resume the default orientation. When pressed, the rendering system 14 moves the imaged volume back to the middle of the volume, and/or resets the cut plane axes to the nominal (starting) orientation.

The volume object 12 provides a method for three dimensional navigation with volume imaging. The orientation of the volume object 12 is sensed. As shown in FIGS. 3 and 4, the orientation of the volume object 12 relative to the imaging system 14, the sensor 16 or the user indicates a viewing direction. The volume object 12 is treated as the volume being viewed by the user. As the volume object 12 changes orientation, the orientation of the volume of data for rendering changes orientation.

Figure 5:
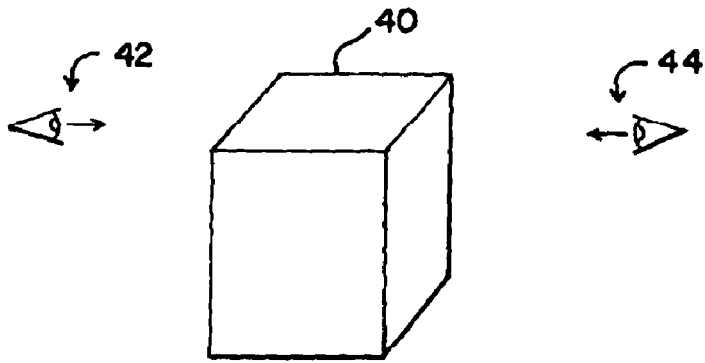
FIG. 5 is a graphical representation of one embodiment of using a volume object representing a viewer's eye for navigation.

In an alternative approach, the volume object 12 is treated as the viewer, such as the eye of the viewer. The 3D representation is rendered as a function of the orientation of the eye of the viewer. FIG. 5 shows the volume 40 representing the data for rendering. The volume 40 is treated as having a static orientation and/or position. When the volume object 12 faces towards the display 18 or imaging system 14 (see viewing direction 42), the volume 40 is rendered from a front viewing direction. When a front of the volume object 12 is away from the display 18 or imaging system 14 (see viewing direction 44), the volume 40 is rendered from a back viewing direction. As the volume object 12 is directed in other directions, other viewing directions are used. Movement or change of position may also be used to control zoom, volume position, and/or cut-planes.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for three dimensional navigation with medical diagnostic ultrasound imaging, the system comprising:
   a handheld volume object;
   a medical diagnostic ultrasound system configured to generate a three dimensional representation of an ultrasonically scanned region; and
   a sensor on the handheld volume object, the medical diagnostic ultrasound system or both the handheld volume object and the medical diagnostic ultrasound system, the sensor configured to determine an orientation in three-dimensions of the handheld volume object, the handheld volume object being handheld during operation of the sensor;

wherein the medical diagnostic ultrasound system generates the three dimensional representation as a function of a viewing angle responsive to the orientation, the volume object representing the scanned region such that the viewing angle is determined as if a user is looking at the volume object as the scanned region where changes in the orientation of the volume object rotate the scanned region, causing rotation of the three dimensional representation in direct correspondence.

2. The system of claim 1 wherein the handheld volume object is free of physical connection.

3. The system of claim 1 wherein the handheld volume object has a greatest diameter of less than six inches.

4. The system of claim 1 wherein the handheld volume object is a clear cube.

5. The system of claim 1 wherein the handheld volume object is shaped, painted or shaped and painted similar to an organ represented by the three dimensional representation.

6. The system of claim 1 wherein the handheld volume object has a clear outer surface with an organ, direction icon or both organ and direction icon within the volume object.

7. The system of claim 1 wherein the sensor comprises an acoustic sensor, an accelerometer, a magnetic sensor, a radio frequency sensor or combinations thereof.

8. The system of claim 1 wherein the sensor is operable to sense distance away from a portion of the medical diagnostic ultrasound system, an amount of zoom relative to the three dimensional representation being a function of the distance.

9. The system of claim 1 wherein the sensor is operable to sense position along the three dimensions, cut-planes of the scanned region selected as a function of the position.

10. The system of claim 1 further comprising:
a user input on the handheld volume object, the user input operable to activate orientation sensing, cut-plane sensing, position sensing, multiplane sensing or combinations thereof.

11. The system of claim 10 wherein the user input comprises a motion activated switch.

12. The system of claim 1 wherein the medical diagnostic ultrasound system generates planes of a multiplanar reconstruction as a function of the orientation.

13. A system for three dimensional navigation with volume imaging, the system comprising:
a volume object with a generally flat outer surface;
an imaging system configured to generate a three dimensional representation of a portion of a patient; and
a sensor configured to determine an orientation in three-dimensions of the volume object;
wherein the three dimensional representation of the portion of the patient is displayed as a function of a viewing angle responsive to the orientation, the viewing angle representing an angle relative to the portion of the patient, the volume object representing the portion such that the viewing angle is determined as if a user is looking at the volume object as the portion where rotation of the viewing object rotates the portion and corresponding three dimensional representation of the portion with a user location being stationary.

14. The system of claim 13 wherein the generally flat outer surface is a cube surface or organ shaped surface without adjustable parts.

15. A system for three dimensional navigation with volume imaging, the system comprising:
a volume object without a tether;
an imaging system configured to generate a three dimensional representation of a scanned region; and
a sensor configured to determine an orientation in three-dimensions of the volume object, the orientation being from a group of orientations including orientations 180 degrees apart;
wherein the three dimensional representation is displayed as a function of a viewing angle responsive to the orientation of the volume object, the volume object representing the scanned region such that the viewing angle is determined as if a user is looking at the volume object as the scanned region where changes in the orientation of the volume object rotate the scanned region, causing rotation of the three dimensional representation in direct correspondence.

16. A method for three dimensional navigation with volume imaging, the method comprising:
providing a handheld volume object having thereon a sensor configured to determine an orientation in three-dimensions of the handheld volume object, the handheld volume object being handheld during operation of the sensor;
sensing an orientation of the volume object, the orientation being from a group of orientations including orientations 180 degrees apart; and
rendering a three dimensional representation of a scanned region as a function of the orientation, the volume object representing the scanned region such that the viewing angle is determined as if a user is looking at the volume object as the scanned region where changes in the orientation of the volume object rotate the scanned region, causing rotation of the three dimensional representation in direct correspondence.

17. The method of claim 16 wherein, when a front of the volume object is towards a display, a volume is rendered from a front viewing direction.

18. The method of claim 16 wherein, when a front of the volume object is away from a display, a volume is rendered from back viewing direction.

19. A system for three dimensional navigation with volume data, the system comprising:
a handheld volume object without a tether;
an imaging system configured to generate an image from the volume data, the image representing a portion of a patient; and
a sensor configured to determine an orientation in three-dimensions of the handheld volume object, the orientation being from a group of possible orientations including orientations 180 degrees apart;
wherein the image is displayed as a function of a viewing angle responsive to the orientation, the viewing angle representing an angle relative to the portion of the patient, the volume object representing the portion of the patient such that the viewing angle is determined as if a user is looking at the volume object as the portion where changes in the orientation of the volume object rotate the portion.

* * * * *